United States Patent [19]
Curtis et al.

[11] Patent Number: 5,958,381
[45] Date of Patent: Sep. 28, 1999

[54] BIS-BIGUANIDE ANTIPLAQUE DENTIFRICE EXHIBITING REDUCED STAINING

[75] Inventors: John P. Curtis, Bloomsbury; Alexander J. Simone, Somerset; Susan Greenfeder, Metuchen; Zehra Siddiqui, Monmouth Junction, all of N.J.

[73] Assignee: Colgate Palmolive Company, New York, N.Y.

[21] Appl. No.: 09/041,452

[22] Filed: Mar. 12, 1998

[51] Int. Cl.$^6$ .............................. A61K 7/16; A61K 7/18; A61K 7/22
[52] U.S. Cl. .................. 424/54; 424/49; 424/52
[58] Field of Search ........................... 424/49–88

[56] References Cited

U.S. PATENT DOCUMENTS

| | | | |
|---|---|---|---|
| 4,487,757 | 12/1984 | Kiozpeoplou | 424/49 |
| 4,565,692 | 1/1986 | Mulvey et al. | 424/49 |
| 5,052,590 | 10/1991 | Ratcliff | 222/94 |
| 5,766,574 | 6/1998 | Christina-Beck et al. | 424/53 |
| 5,776,437 | 7/1998 | Burgess et al. | 424/53 |
| 5,811,080 | 9/1998 | Burgess et al. | 424/53 |
| 5,820,852 | 10/1998 | Burgess et al. | 424/52 |
| 5,820,853 | 10/1998 | Glandorf | 424/52 |
| 5,820,854 | 10/1998 | Glandorf | 424/52 |
| 5,849,269 | 12/1998 | Burgess et al. | 424/52 |

*Primary Examiner*—Shep K. Rose
*Attorney, Agent, or Firm*—Paul Shapiro

[57] ABSTRACT

A dual component chlorhexidine dentifrice composition in which the first component contains a bis-biguanide antibacterial agent and the second component contains an abrasive incompatible with the bis-biguanide, wherein maximum antibacterial effect on dental tissue with reduced staining is achieved when the components and are physically separated prior to use and are mixed upon application to dental tissue.

10 Claims, No Drawings

BIS-BIGUANIDE ANTIPLAQUE DENTIFRICE EXHIBITING REDUCED STAINING

BACKGROUND OF THE INVENTION

1. Field of the Invention

The present invention relates to an oral care composition which contains a bis-biguanide compound effective in the retardation of bacterial plaque accumulation on the teeth and more particularly to a dual component dentifrice composition containing a bis-biguanide compound which achieves plaque reduction with substantially less staining of teeth than normally occurs with bis-biguanide compound containing dentifrices.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infection and dental disease associated with plaque formation. For example, bis-biguanide compounds such as chlorhexidine are well known to the art for their antibacterial activity and have been used in oral compositions to counter plaque formation by bacterial accumulation in the oral cavity. However, it is also well known that bis-biguanide compounds, when used as dental antiplaque agents cause unsightly staining of teeth. Many procedures have been proposed by the art to reduce such tooth staining: U.S. Pat. Nos. 3,925,543, 3,934,002, 3,937,807, 4,051,234, 4,080,441, 4,256,931, 4,273,759 and 4,886,658. However, the presence of bis-biguanide compounds in dentifrice compositions containing conventional ingredients such as abrasives, anionic surfactants and flavorants which are necessary for adequate cleaning and palatability of the dentifrice, these ingredients are normally incompatible with bis-biguanide compounds, and tend to diminish the bioavailability of such compounds necessary for antiplaque efficacy.

There is a clear need in the art to formulate a dentifrice product capable of delivering a bis-biguanide antibacterial agent whereby the other ingredients used to prepare the dentifrice composition do not inhibit the bioavailability of the bis-biguanide compound concomitant with limited tooth staining caused by the compound.

SUMMARY OF THE INVENTION

The present invention encompasses a dual component dental composition which when applied to teeth contains a combination of a bis-biguanide compound, an abrasive and other ingredients normally incompatible with the bis-biguanide compound whereby reduction of plaque is accomplished during tooth brushing with substantially less staining of teeth that normally accompanies the use of dental compositions containing bis-biguanide compounds.

The present invention is based upon the discovery that when a separately maintained bis-biguanide compound containing dental gel component which is free of anionic surfactant and abrasive ingredients and a second abrasive containing dentifrice component, which abrasive is normally incompatible with the bis-biguanide component are simultaneously combined and thereafter applied to the surface of the teeth, an undiminished antiplaque efficacy is unexpectedly obtained with limited staining of teeth when the teeth are brushed with the combined components.

In one embodiment of the present invention, a dual component dental composition of the present invention is provided which is comprised of separate bis-biguanide compound containing gel and an alumina abrasive containing paste components which are housed in a container wherein the components are maintained separate from each other and are not combined and admixed until simultaneous application to teeth is to be performed by the user as by brushing. Unexpectedly, when the separately maintained gel paste components are contacted with each other immediately prior to application to teeth, the ingredients contained in these dental components do not appreciably immediately react to inactivate the antiplaque efficacy of the bis-biguanide compound, thereby allowing the bis-biguanide compound in its full efficacious form, to be applied to the teeth simultaneously with a dentifrice component containing a normally incompatible tooth cleaning abrasive material.

DESCRIPTION OF THE PREFERRED EMBODIMENTS

In the practice of the present invention the dental component containing the bis-biguanide ingredient is formulated as a gel using a vehicle containing a safe and effective amount of bis-biguanide compound such as chlorhexidine in a suitable pharmaceutically acceptable vehicle such as a polyoxyethylene/polyoxypropylene block copolymer.

The bis-biguanide compounds useful in the practice of the present invention are known to the art and a disclosure of such compounds may be found in U.S. Pat. No. 4,886,650 (columns 2–3) which disclosure is herewith incorporated by reference. A bis-biguanide compound preferred for use in the present invention is di($N_1,N_1$'-p-chlorophenyldiguanido-$N_5$, $N_5$')hexane (chlorhexidine) and water soluble salts thereof, including the digluconate and the diacetate salts, especially the digluconate salts. Other salts include the diproponate, the diformate, the dilactate, the dihydrochloride, the dihydrofluoride, the dihydrobromide, the sulfate, the phosphate, the succinate, the pivalate, the citrate, the tartrate and the maleate. Other suitable bis-biguanide compounds include hexetidine, octenidine and alexidine.

The gel compositions useful in the present invention in which a bis-biguanide compound is present, comprise from about 0.001% to about 4% by weight of the bis-biguanide compound.

Polyoxyethylene/polyoxypropylene block copolymers are useful on formulating the vehicle for the bis-biguanide containing gel component of the present invention. Illustrative of the polyoxyethylene/polyoxypropylene block copolymers useful in the practice of the present invention include block copolymers having the formula

$$HO(C_2H_4O)_b(C_3H_6O)_a(C_2H_4O)_bH$$

wherein a is an integer such that the hydrophobic portion (moeity) represented by ($C_3H_6O$) has a molecular weight of about 2750 to 4000, b is an integer such that the hydrophilic portion represented by ($C_2H_4O$) constitutes about 70–80% by weight of the copolymer. Block copolymers of this composition are available commercially under the trademark Pluronic F type. Pluronic F127, which has a molecular weight of 4000 and contains 70% of the hydrophilic $C_2H_4O$ moiety is preferred in the practice of the present invention.

The polyoxyethylene/polyoxypropylene block copolymer is present in present in the bis-biguanide compound containing gel component in an amount within the range of about 10 to about 30% by weight and preferably about 15 to about 25% by weight.

The bis-biguanide dentifrice component is normally prepared in the form of an aqueous gel by suspending the bis-biguanide ingredient in the vehicle and mixing in any suitable mixer, such as a Lightening mixer for about 30 to 60 minutes to form a homogeneous solution from which a substantially rigid, non-fluid gel product is thereby obtained.

The dentifrice component in which an abrasive material is included is generally a paste prepared using a vehicle which contains water, humectant, nonionic surfactant and thickener. The humectant is generally a mixture of humectants, such as glycerin, sorbitol and a polyethylene glycol of a molecular weight in the range of 200–1000, but other mixtures of humectants and single humectants may also be employed. The humectant content is in the range of about 10% to about 80% by weight and preferably about 10–30% by weight. The water content is in the range of about 10 to about 30% by weight.

Thickeners which may be used in the preparation of the abrasive paste component include natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. The thickener may be incorporated in the abrasive containing dentifrice component of the present invention at a concentration of about 0.1 to about 3% by weight and preferably about 0.5 to about 1.5% by weight.

A surfactant is incorporated in the abrasive dentifrice component to provide foaming properties. The surfactant is preferably nonionic, and is included in the abrasive dentifrice component in amounts up to about 3%, and preferably from about 0.05% to about 2% by weight of the composition.

Examples of suitable nonionic surfactants for use in the present invention include condensates of sorbitan esters of fatty acids with ethylene oxide (polysorbates) such as sorbitan mono-oleate with from about 20 to about 60 moles of ethylene oxide. A particularly preferred polysorbate is Polysorbate 20, polyoxyethylene 20 sorbitan monolaurate.

Additional suitable nonionic surfactants useful in the present invention are the condensation products of an alpha-olefin oxide containing 10 to 20 carbon atoms, a polyhydric alcohol containing 2 to 10 carbon atoms and 2 to 6 hydroxyl groups, and either ethylene oxide or a mixture of ethylene oxide and propylene oxide. The resultant surfactants are polymers which have a molecular weight in the range from about 400 to about 1600, contain from about 40% to about 80% ethylene oxide, by weight, and have an alpha-olefin oxide to polyhydric alcohol mole ratio in the range from about 1:1 to abut 1:3, respectively. Other nonionic surfactants useful in the present invention include condensates of sorbitan esters of fatty acids with polyethylene glycol such as sorbitan diisostearate condensed with polyethylene glycol.

Abrasives which may be incorporated in the abrasive containing dentifrice component include alumina and siliceous materials such as silica. Silica abrasives useful in the practice of the present invention are available under the trade designation Zeodent available from J.M. Huber Corp. Alumina abrasives include hydrated alumina, aluminum silicate, calcined alumina and bentonite. The concentration of abrasive in the abrasive dentifrice component of the present invention will normally be in the range of 15 to about 50% by weight and preferably 5 to 40% by weight.

Fluorine-providing salts having anti-caries efficacy may also be incorporated in the abrasive dentifrice component of the present invention and are characterized by their ability to release fluoride ions in water. Among these materials are alkali metal salts, for example, sodium fluoride, potassium fluoride, sodium fluorosilicate, and sodium monofluorophosphate. It is preferable to employ a fluoride salt to release about 10–1500 ppm of fluoride ion.

Any suitable flavoring or sweetening material may also be incorporated in the abrasive containing dentifrice component of the present invention. Examples of suitable flavoring constituents are flavoring oils, e.g., oils of spearmint, peppermint, wintergreen, sassafras, clove, sage, eucalyptus, marjoram, cinnamon, lemon and orange and methyl salicylate. Suitable sweetening agents include sucrose, lactose, maltose, sorbitol, xylitol, sodium cyclamate, perillartine and sodium saccharin. Suitably, flavor and sweetening agents may together comprise from 0.01% to 5% by weight or more of the abrasive containing dentifrice and at such concentrations render the combined gel and dentifrice components with a palatability acceptable to the user.

A striped dentifrice product is obtained in accordance with the practice of the present invention wherein colorants of contrasting colors are incorporated in each of the dentifrice components used in the practice of the present invention, the colorants being pharmacologically and physiologically nontoxic when used in the suggested amounts. Colorants used in the practice of the present invention include pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C # Yellow 15 lake. The pigments have a particle size in the range of 5–1000 microns, preferably 250–500 microns, and are present at a concentration of 0.5 to 3% by weight.

The dyes used in the practice of the present invention are generally food color additive presently certified under the Food Drug & Cosmetic Act for use in food and ingested drugs, including dyes such as FD&C Red #3 (sodium salts of tetraiodofluorescein), FD&C Yellow #5 (sodium slat of 4-p-sulfophenylaxo-B-naphtol-6-monosulfonate), FD&C Green #3 (disodium salt of 4-{[4-(n-ethyl-p-sulfobenzylamino)-phenyl]-4-hydroxy-2-sulfoniumphenyl)-methylene}-[1-(N-ethyl-N-p-sulfobenzyl)-3,5-cyclohexadienimine], FD&C Blue #1 (disodium salt of disulfonic acid of indigotin) and mixtures thereof in various proportions. The concentration of the dye for the most effective result in the present invention is present in the abrasive containing dentifrice composition in an amount from about 0.0005% to about 2% by weight.

It is preferred that the colorant included in the gel component be a dye and that the colorant included in the abrasive containing dentifrice component be a pigment such as $TiO_2$ and that the pigment be of a different color than the dye included in the gel component.

To prepare the bis-biguanide compound containing gel component of the present invention, the humectant and thickener are dispersed in a conventional mixer. Chlorhexidene, a polyoxyethylene/polyoxypropylene block copolymer and color are added and mixed for 30 minutes. The mixture is transferred to a vacuum mixer and mixed for 20–40 minutes under a vacuum mixer in the range of 5 to 100 millimeter of mercury pressure, preferably 5 to 20 mm Hg, providing a homogeneous mixture. The nonionic surfactant and flavor are then added to the mixture which is followed by mixing another 10 to 20 minutes under vacuum of 5 to 50 mm Hg. The resultant product is a non-fluid gel.

To prepare the abrasive containing dentifrice component of the present invention, the humectant and thickener are dispersed in a conventional mixer until the mixture becomes a slurry which is smooth in appearance, after which water is added. This mixture is heated to 100–100° F. and mixed for 10 to 30 minutes producing a homogeneous gel phase. Sweetener and color are added and mixed for 20 minutes. The mixture is transferred to a vacuum mixer and the abrasive is added and mixed for 10 to 30 minutes at high speed under a vacuum in the range of 5 to 100 millimeter of mercury pressure, preferably 5 to 50 mm Hg, providing a homogeneous mixture. The surfactant and flavor are then added to the mixture which is followed by mixing another 10 to 20 minutes under vacuum of 5 to 50 mm Hg. The resultant product is an abrasive dentifrice paste of a texture like that of normal toothpastes having a pH in the range of 5 to 8, preferably 6.5 to 7.5, e.g., 7, and of satisfactory flavor.

The dual component composition of the present invention is packaged in a suitable dispensing container such as a tube or pump in which the components are maintained physically separated and from which the separated components may be dispensed synchronously. Such containers are known to the art. Examples of suitable pump devices are disclosed in U.S. Pat. No. 4,528,180 and U.S. Pat. No. 5,332,124. Examples of a suitable dispensing tube are disclosed in U.S. Pat. No. 4,487,757 and 4,687,663 wherein the tube is formed from a collapsible plastic web and is provided with a partition within the tube defining separate compartments in which the physically separated components are stored and from which they are dispersed through a suitable dispensing outlet.

The following specific Example illustrates the present invention. The individual gel and paste components described below were prepared by following the procedure described above. The amounts of the various ingredients are by weight unless otherwise indicated. The resultant components were packaged in tubes or other containers provided with means for physical separation of the individual dentifrice components.

EXAMPLE

Chlorhexidine Gel

A chlorhexidine containing gel as a component of the dual component antiplaque composition of the present invention was prepared with the following ingredients.

| Ingredients | Wt. % |
| --- | --- |
| Chlorhexidine digluconate (20%) | 9.50 |
| Pluronic F-127 | 20.00 |
| Deionized H$_2$O | 53.25 |
| PEG-600 | 15.00 |
| Polysorbate 20 | 1.20 |
| FD&C Blue #1 1% soln. | 0.30 |
| Flavor (peppermint) | 0.80 |

Abrasive Dentifrice Component

An abrasive containing dentifrice component of the dual component antiplaquue composition of the present invention was prepared with the following ingredients:

| Ingredients | Wt. % |
| --- | --- |
| Deionized water | 26.20 |
| Glycerin | 19.0 |
| Hydroxyethylcellulose | 1.20 |
| Sodium Saccharin | 0.60 |
| Polysorbate 20 | 0.80 |
| Sodium monofluorophosphate | 1.52 |
| Hydrated alumina | 37.88 |
| Alumina oxide | 10.00 |
| Zeodent 165 | 2.00 |
| Flavor | 0.80 |

The chlorhexidine gel and abrasive paste components prepared above were of extrudable consistency. The separate compartments of a multicompartment pump container were filled with the gel and paste components. Ribbons of the two components were extruded synchronously and combined. The combined dentifrice ribbon that was formed was evaluated for antibacterial efficacy in vitro against S. mutans, a microorganism present in human plaque, by the short interval killing test (SIKT) method.

The SIKT test is an in vitro anitmicrobial test which incorporates a fixed contact time wherein 1 ml of dental treatment composition diluted with water is mixed with a predetermined inoculum of bacteria ($10^6$–$10^7$) colony forming unit, (cfu/ml) for a 1–2 minute contact time. The system is then neutralized to inhibit further antibacterial activity. The surviving bacteria are enumerated using plate count methodology. The reduction in cfu counts compared to a water control is the basis for expressing antibacterial activity of the agents. The results of the SIKT test are recorded in Table I. For the purposes of comparison, a commercially available antibacterial mouthrinse containing 0.12% by weight chlorhexidine was digluconate used as a comparative composition.

TABLE I

| | Log Reduction in Bacterial Colonies (S. mutans)/ml | |
| --- | --- | --- |
| Composition | 1:1 dilution | 1:2 dilution |
| Dentifrice | >4.5 | >4.5 |
| Mouthrinse | 4.4 | 1.4 |

The results recorded in Table I indicate that the antibacterial activity of the chlorhexidine in the dual component dentifrice was not impaired, when the abrasive and antibacterial compounds of the dual component dentifrice remain separated until dispensed together simultaneously for application to the teeth, the antibacterial efficacy of the dual component dentifrice of the present invention being at least equal to the commercial chlorhexidine mouthrinse.

Tooth Staining Study

In a two month pilot study to evaluate staining as well as product efficacy by the dual component chlorhexidine dentifrice composition of the present invention, 20 patients were randomly assigned to one of two treatment groups, one group of 10 subjects brushed their teeth with a conventional fluoride toothpaste followed by a commercially available chlorhexidine rinse containing 0.12% chlorhexidine gluconate by weight. The second group used only the chlorhexidine dentifrice of the Example. Product efficacy was clinically assessed using standard scoring methods namely Plaque Index (Quigley-Hein [Turesky Modification]) and Gingival Index (Loe-Silness). Stain intensity was evaluated according to the method of Lobene, R. R. Journal of the American Dental Association, Vol. 77, pages 849–855, October 1968, "Effects of Dentifrices on Tooth Stains with Controlled Brushing". Stain intensity was evaluated for both the gingival region of the tooth (i.e., near the gum line) and for the body or facial portion of the tooth (excluding the crown). The scoring criteria was as follows:

| Score | Description |
|---|---|
| 0 = | No stain |
| 1 = | Light Stain - yellow tan |
| 2 = | Moderate stain - medium brown |
| 3 = | Heavy stain - dark brown/black |

The combined components of the chlorhexidine dentifrice of the Example and the commercial chlorhexidine mouthrinse were found to be similarly efficacious against plaque, gingivitis and plaque microflora confirming the results of the SIKT test. The results of the stain intensity evaluation are recorded in Table II below and indicate that there was a very strong trend in the chlorhexidine dentifrice of the Example towards less severe staining of the teeth as compared to the commercial chlorhexidine mouthrinse.

TABLE II

AVERAGE STAIN INTENSITY SCORE

|  | PHASE | DENTIFRICE | MOUTHRINSE |
|---|---|---|---|
| GINGIVAL SCORE | Baseline | 0.238 | 0.713 |
|  | 2 weeks | 0.275 | 0.675 |
|  | 4 weeks | 0.328 | 0.725 |
|  | 8 weeks | 0.250 | 0.950 |
| BODY SCORE | Baseline | 0.163 | 0.300 |
|  | 2 weeks | 0.225 | 0.363 |
|  | 4 weeks | 0.172 | 0.400 |
|  | 8 weeks | 0.334 | 0.525 |

What is claimed is:

1. A dual component bis-biguanide dental composition exhibiting reduced staining to teeth in which a first component is an extrudable gel containing a bis-biguanide antibacterial agent and is free of an abrasive and a second component is an extrudable paste free of bis-biguanide antibacterial agent and containing an abrasive incompatible with the bis-biguanide agent, the first and second components being synchronously extrudible when dispensed for application to the teeth, the first and second components being physically segregated prior to use, the components when mixed upon application to teeth providing undiminished antiplaque efficacy to dental tissue with less staining of teeth than normally occurs with bis-biguanide compound containing dentifrices.

2. The composition of claim 1 wherein the abrasive is hydrated alumina.

3. The composition of claim 1 wherein the abrasive is silica.

4. The composition of claim 1 wherein the abrasive is aluminum oxide.

5. The composition of claim 1 wherein the bis-biguanide is chlorhexidine.

6. A method for the antibacterial treatment of teeth which comprises preparing a dual component dentifrice composition in which a first component is an extrudable gel composition containing a bis-biguanide antibacterial agent compound and is free of an abrasive in the first component and a second component is an extrudable paste composition containing an abrasive and free of bis-biguanide antibacterial agent maintaining the first component physically separated from the second component, synchronously extruding the first and second components and then mixing the extruded components upon application to the teeth whereby undiminished antiplaque activity with less staining of teeth then normally occurs with bis-biguanide compound containing dentifrices is obtained.

7. The method of claim 6 wherein the abrasive is hydrated alumina.

8. The method of claim 6 wherein the abrasive is silica.

9. The method of claim 6 wherein the abrasive is aluminum oxide.

10. The method of claim 6 wherein the bis-biguanide compound is chlorhexidine.

* * * * *